US006644317B1

(12) United States Patent
Lawton

(10) Patent No.: US 6,644,317 B1
(45) Date of Patent: Nov. 11, 2003

(54) CLOSE CONTACT DRAPE

(76) Inventor: Rustalyn Lawton, 6362 Calle Montalvo Cir., Granite Bay, CA (US) 95746

( * ) Notice: Subject to any disclaimer, the term of this patent is extended or adjusted under 35 U.S.C. 154(b) by 0 days.

(21) Appl. No.: 10/213,520

(22) Filed: Aug. 8, 2002

(51) Int. Cl.[7] ............................................. A61B 19/00
(52) U.S. Cl. ......................... 128/849; 128/853; 2/49.2
(58) Field of Search .................. 128/849–853, 128/845, 846, 874, 875; 2/49.2, 49.4, 52

(56) References Cited

U.S. PATENT DOCUMENTS 4,581,752 A * 4/1986 De Luca ....................... 2/267
4,924,527 A * 5/1990 Hintermayer ................ 2/49 R
4,938,233 A * 7/1990 Orrison ....................... 128/853
5,509,141 A * 4/1996 Saltman ........................ 2/49.2
5,682,609 A * 11/1997 Ayo ............................. 2/49.2
6,219,846 B1 * 4/2001 Toole ............................ 2/52

* cited by examiner

Primary Examiner—Michael A. Brown
(74) Attorney, Agent, or Firm—Mark C. Jacobs

(57) ABSTRACT

A close contact drape to be placed upon the front of the body from neck to above the knees to cover the body. The drape is secured behind the neck by interconnecting flaps using a closure. The drape is made of flexible cloth and has three laterally spaced pockets located at what is the chest area of the average female wearer. In each pocket there is disposed a flexible sheet plastic panel. Tactile sensation of a touching of the soft tissue of the human breast by a service provider is inhibited or prevented by the presence of the plastic panels overlying the chest area of the wearer of the drape.

10 Claims, 2 Drawing Sheets

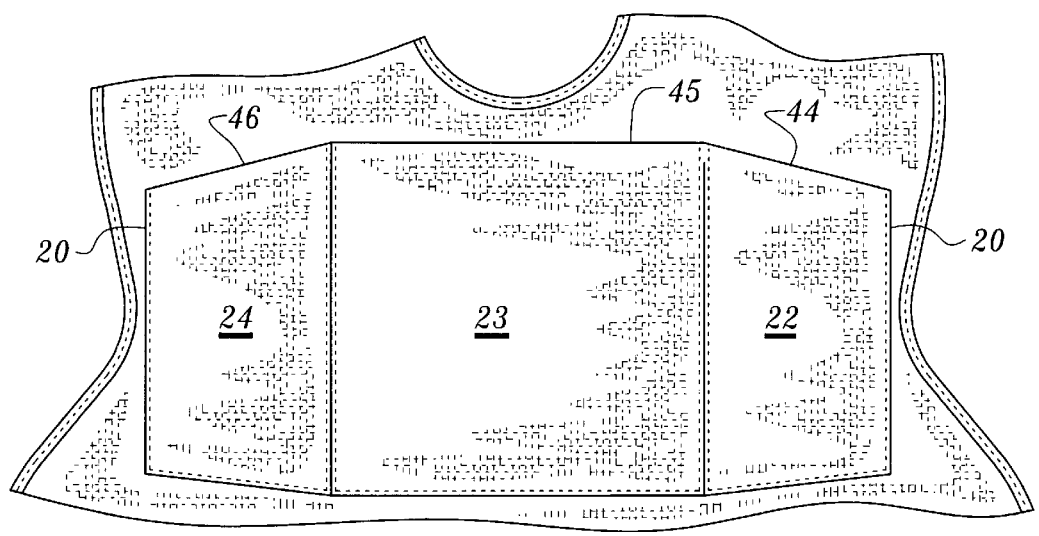
Fig. 3
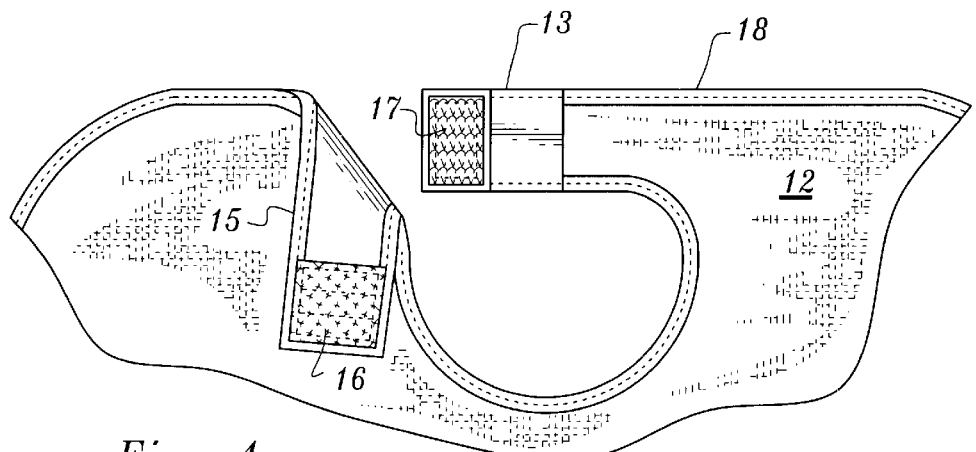
Fig. 4
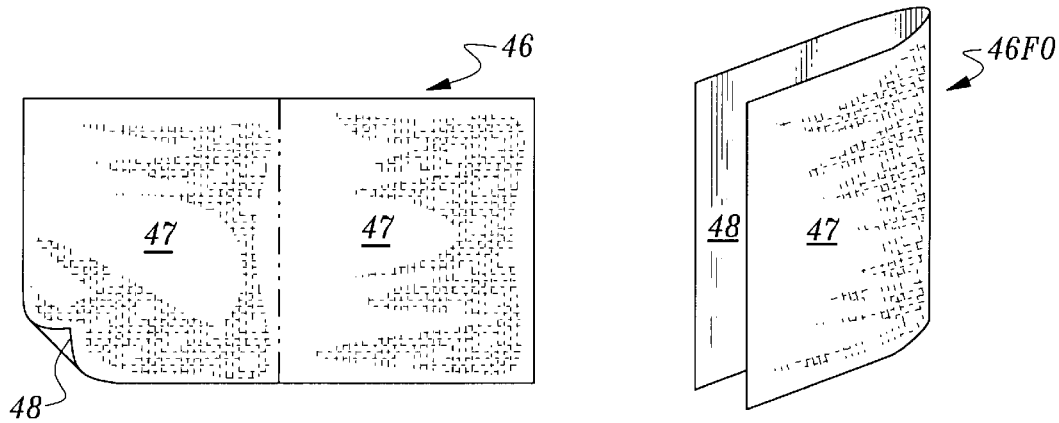
Fig. 5
Fig. 6

CLOSE CONTACT DRAPE

FIELD OF THE INVENTION

This application relates to a partial body covering to be used by dentists, opticians, dermatologists, and other professionals who work closely with their clients or patients. The drape is intended to eliminate the opportunity or chance of touching the patient's chest that could lead to a vicarious tactile sensation.

BACKGROUND OF THE INVENTION

In today's litigious world more and more opticians, ophthalmologists, dentists, makeup artists, and other professionals who work closely with their patients as opposed to "at arms' length" are being charged falsely with "unwanted touching of bodily parts."

Cosmetologists use drapes and dentists use a bib but the beauty shop apron or the barber shop aprons are just that. This one-piece light fabric, usually cotton or polyester, is placed over the customer's thorax to keep clothing free of cut hair. Dentists use a bib much like the bib people receive in a restaurant when eating lobster.

Problems arise in several arenas. First, for dentists who often place instruments on the patient's chest for either convenience or timeliness of access for complex dental work. Makeup artists often have clients' in a particularly reclined position for easier access to the face. The chances of touching the chest area of a female, especially a well-endowed one, with the elbow or wrist are quite high whether intentional, or as more than likely, unintentional. The same is true for opticians and ophthalmologist who often work in low lit rooms with patients in a seated or semi-reclined position.

The purpose of the device of this invention is to protect both the patient and customer from unwanted touching and to protect the professionals from unfounded charges. In short, the close contact drape of this invention presents a psychological barrier for the benefit of both the wearer and the worker, and a physical impediment to the tactile sensation of touching soft tissue, whether done accidently, unknowingly, or intentionally.

The invention accordingly comprises the device possessing the features, properties, the selection of components which are amplified in the following detailed disclosure, and the scope of the application of which will be indicated in the appended claims.

For a fuller understanding of the nature and objects of the invention, reference is made to the following detailed description, taken in conjunction with the accompanying drawings.

SUMMARY OF THE INVENTION

A heavy fabric drape conveniently built of flexible panels sewn or otherwise retained in a permanent position, whose location is specifically chosen, such as to inhibit any tactile sensation, vicarious or otherwise, of a worker to the wearer's chest area.

It is a first object of the invention to provide a body drape that covers the body from the neck to the lap area. The drape is shaped to permit full arm movement and is secured around the neck by hook and loop closure [e.g., Velcro®] to retain it in the desired location.

It is another object of this invention to provide a drape having built-in flexible panels that inhibit tactile sensation normally derived from a touching of the human body in areas in which the panels within the drape overlie the body.

It is a third object of the invention to provide an easy to clean protection drape that can be wiped to remove soiling, dirt, and debris, sterilized and folded for storage until it is again needed for use.

It is a fourth object of the invention to provide a lightweight reusable chest protection drape for use by but not limited to opticians, dentists, physicians, makeup artists, and hair designers.

It is a fifth object of this invention to provide a device to inhibit the potential claims of unwanted physical touching being made by persons being treated against the professional provider.

Other objects of the invention will in part be obvious and will in part appear hereinafter.

BRIEF DESCRIPTION OF FIGURES

FIG. 3 is a closeup view of the panel area from the reverse side of the drape.

FIG. 4 is a closeup view of the preferred closure system utilized to secure the drape around the neck of the wearer.

FIG. 5 is a diagrammatic view of a section of material utilized to make one of the panel pockets forming a part of this invention.

FIG. 6 a diagrammatic view later in time of the same section of material ready to be sewn into position.

KNOWN PRIOR ART

Applicant's counsel is familiar with the following patents, none of which are deemed very relevant to the invention at hand.

| Ashcraft | 4,660,224 | Apr. 28, 1987 |
| Johnson | 3,995,321 | Dec. 7, 1976 |
| Brown | 3,286,279 | Nov. 22, 1966 |

DESCRIPTION OF THE PREFERRED EMBODIMENT

Figure 1:
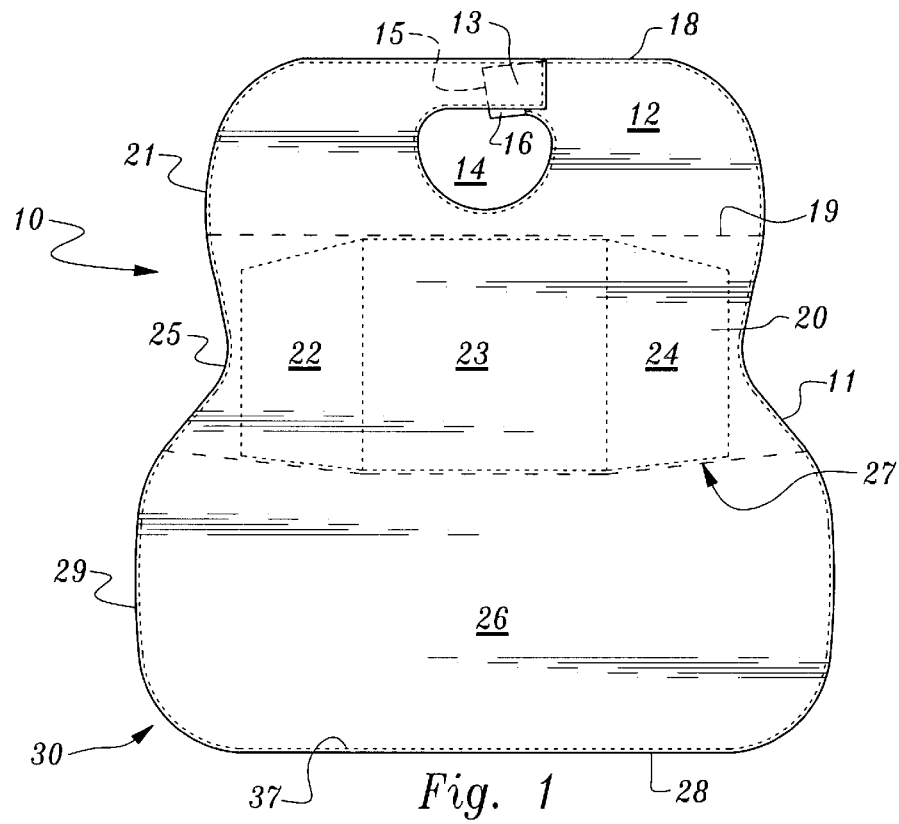
FIG. 1 is a top plan view of the obverse side of the close contact drape of this invention.

Reference is first made to FIG. 1. Here it is seen that the invention 10 is an essentially one-piece integrated drape whose main portion 11 has a front face 30, and a rear face 31 [FIG. 2]. The drape 10 fits over the thorax of the body from the neck down to the lap area of most people. The main portion 11 of a modified violin shape formed by three integrated sections that form one garment. These are the upper section 12, the middle section 20 and the lower section 26. The device 10 is retained in place around the neck of the wearer by first and second integrated flaps 13 and 15. Note the presence of the circumscribing seam or stitching, 37, better seen in FIG. 2.

The main body 11 comprises the upper section 12 which commences at the top edge 18 and terminates at the imaginary dashed line 19 and is of a generally tilted C-shaped configuration, with the two appendages of the C being inwardly directed opposed overlapping flaps 13 and 15. An opening 14 is defined within the tilted C through which the wearer's head fits. The two flaps matingly engage as shown here due to the presence of a two-part closure such as a hook and loop type sold under the Velcro® brand, a portion of which 16 is on the outer surface of one flap 13 and the other portion of which 17 is on the interior surface of the other flap 15. There is no criticality either to the exact shape or dimension of the neck opening, so long as it is generally universal, and vertically ends at what would be the first button position on an open collar shirt; i.e., just below the throat.

The imaginary line 19 and the top edge 18 of the upper section are substantially parallel to each other. The two sidewalls or edges 21 of the upper section is a mirror image slightly convex arcs.

The middle section, 20, defined as being between the imaginary line 19 and the spaced down from 19 second imaginary line 27, parallel thereto is of a configuration that resembles a bustle, in that the side wall 25 tapers downwardly from the terminus of the sidewall 21 of the upper portion and then outwardly beyond the edge of the lateral extension of the upper portion.

Whereas the upper section is formed only of one layer of fabric such as polyvinyl chloride film, with a flocked or non-woven backing thereupon and the relevant closure, the middle section while flat on the front face includes three internal patch pockets 22,23, and 24 all of which are attached to the rear face and are one time accessible from the rear face 31. Two of the internal patch pockets 22 and 24 are mirror image side facing trapezoids while the center one 23 is essentially square. The details of the pockets and the access and use thereof will be discussed infra with respect to FIG. 2.

The lower section 26 of the drape 10 is essentially rectangular with chamfered lower outer corners. The side wall or edge is designated 29, the lower edge 28 and the upper edge thereof are imaginary line 27 which coincides with the bottom edge of the middle section. This section also is only single layer fabric with a backing.

Figure 2:
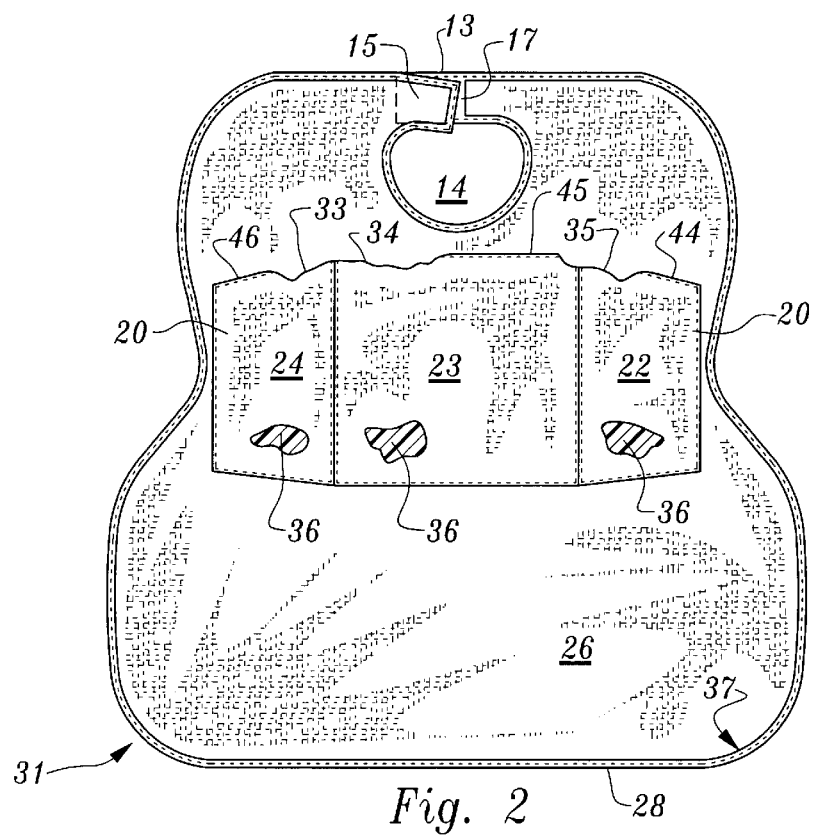
FIG. 2 is a top plan view of the reverse side thereof.

For reinforcement purposes, a seam 37, as noted in this Figure and in FIG. 2, is formed around the entire periphery of the drape for reinforcement purposes. The seam is formed by bending and overlapping ¼ to ½ inch of material and then stitching along the edge thereof to bind the material and to prevent wear.

Turning to FIG. 2, the two flaps, 13 and 15, are seen from the rear. Also, visible in this view is a male portion of Velcro closure 17 on one of the flaps, the left flap as seen from the front of the device.

The cutaway areas 33, 34, 35, all illustrate open edges of the three insert pockets 22, 23, 24, as noted previously with respect to FIG. 1. Reference to FIG. 2 brings the attention of the reader to the fact that the numbers 22 and 24 are reversed in FIG. 2.

Pockets 22, 23, 24 are noted on the obverse face of the drape of this invention in FIG. 1 for ease of reference. In reality however, they are formed on the reverse face 31. Reference is made to FIGS. 5 and 6. A section of material 46 of the nature used for the body of this invention, having a backing side 47 and a film side 48 is cut out with either the length or width being double in dimension. This section 46 of twice the correct dimension in one direction is folded over in half upon itself along the double dimension direction, to give a double thick piece of material with the backing layer 47 as the external face as per FIG. 6. This now folded over section 46FO so designated in FIG. 6, is sewn into place over the backing of the fabric forming the rear face 31 of the main body 11 at the desired locations. Of course, it is understood that the illustrations of FIGS. 5 and 6 show fabric sections configured for the central pocket. The fabric for the outer pockets would be trapezoidal in configuration. When these pieces of fabric 46 are overlaid and sewn into position, one edge 44, 45, and 46 is left unsewn until the plastic panel is inserted into position See FIG. 2.

In each of the insert pockets 22, 23, 24, there is disposed a piece of reinforcing but flexible plastic sheet material, preferably poly propylene sheet 36. Each panel, which optionally may have chamfered corners, is cut in size and shape to fit in each of each pocket 22, 23, 24 through the unsewn area referred to infra. The upper edge of each of these three pockets 44, 45, 46, of pockets 22, 23, 24, is then stitched once the insert 36 is put in position. The seam when completed, now encloses the respective panel and retains the insert material in a fixed position within the respective pocket. See also FIG. 3. Styrene, and polyethylene flexible sheets can also be employed.

The configuration of the three inserts, is seen in FIG. 3, was specifically chosen such that each of the three pockets is closely adjacent to the next pocket and each contains its own individual insert of plastic, such that the drape will free flow around the curvature of the body of the wearer, be the wearer be male or female. The zone of protection of these inserts is intended to be the chest/breast area of the average male or woman. The trapezoidal shape of the pockets 22 and 24, and the respective insert channels that go into the trapezoidal pockets 22 and 24 is deemed significantly beneficial because of the flexibility that is afforded the wearer, and the wearer's ability to move the arms to permit the arms of the wearer to overlay the drape 10 with significant comfort. The use of a one piece section of plastic across the entire width of the body did not lend the degree of comfort obtained when three individual panels were employed.

The material used for the body of this invention, other than the sheet plastic inserts, is preferably a flexible vinyl film having a non-woven backing, and which is similar to that used for vinyl tablecloths. This material is a vinyl film, textured if so desired to simulate leather, decorated in any pattern, solid or multicolor, as may be desired, is backed with a conventional cotton or other non-woven backing for the rear face 31. This low cost backing known to the art, for its anti-static quality also provides bulk and ease of handling, and additionally prevents slippage off the body of the patient/customer. The backing also contributes to the comfort of the wearer as vinyl films in contact with the skin do not breathe and cause sweating. Of course other flexible fabrics having a suitable backing and adequate mass can be used, including but not limited to polyester and nylon since they too are machine washable.

It is seen from an inspection of FIGS. 1 and 4, that the two flaps 13 and 15 extend toward each other from appropriate locations around the neck opening 14. Each of these flaps, 13,15 includes a Velcro® portion 16 or 17 sewn, glued or otherwise applied to the terminus of the flap. As can be seen, the flaps are formed from extended sections of the same material as the rest of the drape. These extended sections are folded and stitched in place along seam 40 such that the obverse side of the fabric is external for both the front and rear of the flaps 13, 15. See FIG. 4. The mating engagement of the two Velcro portions serve to provide a closure means for retaining the two flaps behind the back of the neck of the wearer through the opening 14. Other closure means such as mating snaps or even a hook and eye closure or a button and button hole can be utilized.

MANUFACTURE OF THE DEVICE OF THIS INVENTION

I experimented in order to find suitable dimensions for the various areas of the device. The dimensions can be varied both upwardly and downwardly to accommodate wearers of different physical sizes. The following dimensions were found to be the most universally acceptable for comfort. Total elevation is preferably about 36 inches. As can be seen the width varies in that the width below the inserts 36 is about 32½ inches wide for the bottom section 26, whereas the minimum width between the two sidewalls 25 is about 25 inches wide for the middle section 20. The measurement at the elevation across the bottom of the neck opening laterally is about 27½ inches. Each of the trapezoidal pockets 22 and 24 are seen to be about 6 inches by 9½ inches by 11½ inches for the interior vertical edge, and the center pocket is approximately 11 by 11. The spacing between pockets laterally is about ¼ to ½ inch. Each flap 13, 15 is approximately 3 inches high and 3½ inches wide. The neck opening is disposed spaced up from the central insert by about 2½ inches. This means that the pocket 23 is approximately 10½ inches from the top edge 18 of the device.

The actual cutting out of the fabric, the edge stitching, the formation of the flaps and the creation of the pockets for the insert panels is well within the skill of the art of a seamstress or tailor.

USE AND PURPOSE OF THE APPARATUS

Drapes and bibs are well known for use in dental offices covering. In the case of dentists carrying out certain procedures, they sometimes place instruments on the covering of the patient's body, especially when working within time constraints. Bibs and drapes are also known for use by barbers, and hair stylists and in a different format, by certain physicians. These coverings are NOT used very often by such professionals as optometrists, or opticians since generally the purpose of the drape, bib or other covering is to keep dirt and debris off of the lap or chest of the patient-customer, who is the wearer of the covering. The persons providing the services be they a doctor, dentist or hair stylist, as a class shall be designated as PROVIDERS. The party being worked upon, shall as a class be designated as the WEARER.

The invention at hand is intended for the protection of the PROVIDER and quite secondarily for the prevention of dirt and debris from accumulating on the wearer. The purpose of the invention is to inhibit the basis for unfounded charges of unwanted touching most especially by female wearers against male providers.

The device of this invention is designed to specifically remove any vicarious thrill that could be received by a provider, usually a male, from the rubbing or touching of the soft tissue of primarily female wearers. The plastic panels disposed in the pockets are specifically designed to be flexible, for curvature around the upper body of variously configured wearers, be they male or female. Tactile sensation of the touching in the chest area is inhibited by the sheet plastic panels disposed in the drape because when properly worn; the chest area is overlaid by the panels. Thus a touching even unintended, would not be felt by the wearer due to the interposition of the panels disposed within the drape.

As to the lower genitals, only the thickness of the fabric covers the lower genitals, but that is generally enough, for several reasons. First, in females the vagina is recessed and so an unintentional act of touching would provide little or no tactile sensation due to the usual presence of the clothing with the drape overlaid, thereby preventing any type of possible digital manipulation. Secondly, the mis-perception of improper touching does not take place very often at the lower genitals, as the provider is usually working upon or treating the upper body or facial area.

By having the drape of this invention present upon the body front of the wearer, should an accidental contact of the chest area be made, the mis-perception of the intention of such accidental contact is alleviated and a sense of security is provided to the wearer because the potential for tactile sensation of soft tissue is prevented. Thus while an unintended contact may be made by the provider, during such as but not limited to, the trimming of eyebrows; the filling of a rear tooth where light upon the tooth is difficult to come by; the removal of debris from an eye or even the fitting of glasses, the wearer will not jump to a wrong conclusion that the touching was an act of intentional misconduct, as the sense of security provided by the drape of this invention, removes the potential for vicarious thrills to the provider, and eliminates any feeling by the wearer of possible breast manipulation or fondling.

As with a dental x-ray drape, which is quite heavy and uncomfortable due to the presence of the lead shielding, the drape of this invention is light weight and comfortable for extended periods of time. It is placed over the body and the two flaps are connected by the preferable Velcro® closure behind the neck.

It is seen that I have developed a drape that provides a sense of body security especially to female wearers, in that any feeling that could be achieved from an improper touching by a service provider is at least inhibited if not eliminated. And, at the same time, should an accidental touch transpire, the wearer is given the security of knowing that the mere presence of the drape indicates the state of mind of the provider in wanting to avoid any mis-perception of illegal conduct, especially if a totally innocent unintended touching does indeed transpire.

Thus, the invention protects both the wearer and the provider. The wearer is protected from physical abuse or harassment by the provider and the provider is protected from the mental anguish associated with wrongful charges of indiscretion. The unit can be washed off with a cloth should any debris or dirt come in contact with it, and sterilized accordingly. Of course, use of the drape of this invention does not preclude the use of a small paper or film bib around the neck of the wearer partially overlying this invention.

Since certain changes may be made in the described device without departing from the scope of the invention herein involved, it is intended that all matter contained in the above description and shown in the accompanying drawings shall be interpreted as illustrative and not in a limiting sense.

I claim:

1. A drape to be placed over the body from neck to above the knees, and which is secured by integrated flaps that fasten behind the neck of the wearer, which drape comprises:
    a main body having an obverse face and a reverse face, the body having three integrated sections;
    a first and upper generally tilted C-shaped section, with appendages of the C forming a neck opening and being inwardly directed opposed overlapping flaps, said flaps each having a portion of a closure thereon for matingly engaging the two flaps behind the neck of a wearer;
    a second and middle section disposed below and integrally connected to the longest dimension of the upper section and of a configuration that resembles a bustle, by having opposed side walls that taper downwardly from the terminus of the upper section and then outwardly beyond an edge of a lateral extension of the upper portion;

a third lower section which is disposed below and integrally connected to the middle section, and which is essentially rectangular; and said middle section having a trio of laterally adjacent but separate sewn up patch pockets, attached to the rear face of the drape, in each of which pockets is disposed a flexible plastic sheet, said sheets generally overlying the human chest area of a wearer when the drape is placed over the body of a wearer and secured behind the neck of the wearer.

2. The drape of claim 1 wherein the flexible plastic sheet is polypropylene.

3. The drape of claim 1 wherein the trio of pockets of the second section are two opposed trapezoidal pockets with a rectangular pocket disposed between the two trapezoidal pockets; and wherein the plastic sheet is sized to fit and of the shape of the pocket.

4. The drape of claim 1 wherein the material used for the body of the drape is polyvinyl chloride film having a non-woven backing.

5. The drape of claim 4 wherein the length of the drape is about three feet long.

6. The drape of claim 1 wherein the corners of the third lower section which is generally rectangle, the corners are chamfered.

7. The drape of claim 1 wherein the material for the body is a washable fabric selected from the group consisting of any water cleanable polyester, acrylic, or nylon containing fibre.

8. The drape of claim 1 wherein the material for the body and the patch pockets is polyvinyl chloride having a non-woven backing, and further including a peripheral seam to enhance the cosmetics of the drape.

9. A drape to be placed over the body from neck to about the knees, and which is secured by integrated flaps that fasten behind the neck of the wearer, which drape comprises:

a main body having an obverse face and a reverse face, the body having three integrated sections;

a first and upper generally tilted C-shaped section, with appendages of the C forming a neck opening and being inwardly directed, opposed overlapping flaps, said flaps each having a portion of a closure thereon for matingly engaging the two flaps behind the neck of a wearer;

a second and middle section disposed below and integrally connected to the longest dimension of the upper section and of a configuration that resembles a bustle, by having opposed side walls that taper downwardly from the terminus of the upper section and then outwardly beyond an edge of a lateral extension of the upper portion;

a third lower section which is disposed below and integrally connected to the middle section, and which is essentially rectangular, and has chamfered corners;

said middle section having a trio of laterally adjacent but separate sewn up patch pockets, two of which are trapezoidal in configuration and a rectangular /square one disposed therebetween, all of which are attached to the rear face of the drape, in each of which pockets is disposed a flexible plastic sheet, said sheets generally overlying the human chest area of a wearer when the drape is placed over the body of a wearer and secured behind the neck of the wearer; and wherein the closure for the two flaps is a hook and loop closure.

10. The drape of claim 1 wherein the closure for the two flaps is a hook and loop closure.

* * * * *